US006256089B1

(12) United States Patent
Baker

(10) Patent No.: US 6,256,089 B1
(45) Date of Patent: Jul. 3, 2001

(54) OPTICAL DONOR TISSUE CELL

(75) Inventor: Phillip C. Baker, Orinda, CA (US)

(73) Assignee: Eyetech Vision, Inc., La Jolla, CA (US)

( * ) Notice: Subject to any disclaimer, the term of this patent is extended or adjusted under 35 U.S.C. 154(b) by 0 days.

(21) Appl. No.: 09/464,110

(22) Filed: Dec. 16, 1999

(51) Int. Cl.[7] .............................. G01N 21/00; G01N 1/10
(52) U.S. Cl. .............................................. 356/73; 356/247
(58) Field of Search ............................. 356/73, 244, 246, 356/124, 125; 206/5.1

(56) References Cited

U.S. PATENT DOCUMENTS 3,769,963 11/1973 Goldman et al. .................... 128/2 R
3,985,445 * 10/1976 Tagnon ................................ 356/125
4,277,172 * 7/1981 Richards ............................. 356/244
4,496,243 * 1/1985 Machida .............................. 356/244
4,538,608 9/1985 L'Esperance, Jr. ............... 128/303.1
4,781,453 11/1988 Kobayashi ........................... 351/205
4,844,242 * 7/1989 Chen et al. ........................... 206/5.1
5,019,084 * 5/1991 Aysta et al. .......................... 606/107
5,956,123 * 9/1999 Abe et al. ............................ 351/216

* cited by examiner

*Primary Examiner*—Frank G. Font
*Assistant Examiner*—Michael P. Stafira
(74) *Attorney, Agent, or Firm*—Nydegger & Associates

(57) ABSTRACT

A sample cell for imaging a tissue sample includes a base member formed with a pedestal and a base window. A retainer ring is engaged with the pedestal to retain the tissue sample on the pedestal. A housing with a housing window is engageable with the base member to create a fluid chamber and establish an optical path extending through the base window, tissue sample, retainer ring and housing window. A light source directs a first light beam along the optical path to illuminate the tissue sample. Also, an optical detector outside the housing window receives the first light beam after it has be transmitted through the tissue sample. Additionally, the housing has a side window distanced from the optical path and oriented at an angle, α. A second light beam configured as a slit having a length that extends across the breadth of the tissue sample and a width that is approximately equal to the depth of the tissue sample can separately illuminate the tissue sample. Light in this second beam is scattered by the tissue sample and is detected through the side window. A computer is connected with the optical detectors to analyze the material properties of the tissue sample.

20 Claims, 2 Drawing Sheets

OPTICAL DONOR TISSUE CELL

FIELD OF THE INVENTION

The present invention pertains generally to cells for holding harvested donor tissue samples before they are to be used for transplant surgery. More particularly, the present invention pertains to donor tissue holding cells which allow the tissue sample to be measured and evaluated in the cell for purposes of determining its suitability for transplant surgery. The present invention is particularly, but not exclusively, useful as a donor tissue holding cell which is adaptable for use in optical procedures and techniques to measure and evaluate the suitability of donor corneal tissue for transplant surgery.

BACKGROUND OF THE INVENTION

Specialized organ donor programs have been implemented in the U.S. and other countries with varying degrees of success. Perhaps the most important concern of any organ donor program is the availability of organs. At the next level, however, there is an equally important concern that the donor organ tissue be suitable for the intended use. Specifically, it is necessary for the donor tissue to be suitable for transplant surgery.

In the particular case where the donor tissue is tissue from the cornea of a donor eye, the question of suitability for purposes of transplant surgery is actually two-fold. First, it is necessary for the healthcare professional to assess information about the donor tissue which will assure there is a suitable match between the donor and the recipient. Here, the obvious reason for having a good match is that there will be a more effective surgical outcome with consequent better patient response and recovery. Second, it is also necessary for the healthcare professional to know the precise dimensions and shape (refractive properties) of the eye. Such knowledge not only allows better control of the tissue interface between the donor tissue and the recipient during surgery, it also leads to a better post-surgical visual outcome. Specifically, insofar as the post-surgical visual outcome is concerned, it is important that the necessary refractive corrections provided by the donor corneal tissue be precisely controlled relative to the pre-surgical condition of the recipient.

When assessing corneal tissue for its suitability for transplant surgery, several considerations must be taken. For one, it is important to assess and evaluate the health of the donor tissue. This can be done by evaluating the extent, if any, to which the cornea may have been earlier affected by corneal scarring or corneal disease. It is well known that such an evaluation can be done using optical techniques. Additionally, as another consideration, it is important to assess the material properties of the donor tissue. Specifically, material properties of a cornea such as density, amorphousness, crystallinity, and transparency can affect the suitability of the corneal tissue as a candidate for transplant surgery. It is also well known that such an evaluation can be accomplished using optical interference techniques.

The present invention recognizes that the surgical suitability concerns mentioned above with regard to corneal tissue can be addressed if the donor tissue is appropriately accessible. Appropriate accessibility, however, requires that the donor corneal tissue be properly preserved and that it not be unduly disturbed during evaluation. Further, due to the fact that many material properties involve optical measurements and evaluations of the cornea, accessibility also requires that the donor corneal tissue be appropriately positioned for illumination by light beams and for evaluation by optical detectors.

In light of the above, it is an object of the present invention to provide a sample cell which can be used to image a tissue sample for purposes of screening the sample to identify compromised donor corneal tissue. Another object of the present invention is to provide a sample cell for use in imaging a tissue sample which is adaptable for imaging the sample using both transmitted light and scattered light. Still another object of the present invention is to provide a sample cell for use in imaging a tissue sample which is allows the tissue sample to be measured both for its physical dimensions as well as for its material properties. Yet another object of the present invention is to provide a sample cell for use in imaging a tissue sample which is easy to use, relatively simple to manufacture, and comparatively cost effective.

SUMMARY OF THE PREFERRED EMBODIMENTS

In accordance with the present invention, a sample cell for use in imaging a tissue sample includes a base member which is formed with a pedestal. Further, the pedestal is formed with a base window which acts as a surface for supporting the tissue sample, and the pedestal is formed with a small circular ridge which surrounds the base window (surface) to help maintain the position of the tissue sample on the pedestal. Additionally, the sample cell includes a retainer ring which is engageable with the pedestal, and which acts with the ridge to retain the tissue sample on said pedestal. Importantly, the pedestal and the retainer ring act together to establish a "non-influencing" hold on the tissue sample. Stated differently, the tissue sample is retained, but is not restrained, by the combination of the pedestal and retainer ring.

A housing, which is formed with a housing window, is engageable with the base member to create a vented fluid chamber between the housing and the base member. More specifically, when the housing is engaged with the base member, the pedestal extends into the chamber. Consequently, as the chamber is filled with an appropriate fluid, such as a saline solution, the tissue sample will be bathed in the solution. Also, upon engagement of the housing with the base member, a straight optical path is established through the sample cell which extends sequentially through the base window, the tissue sample, the retainer ring and through the housing window.

A light source is provided for the sample cell of the present invention which is capable of producing a sheared beam of collimated light. Importantly, the light should have a wavelength which will allow the light to pass through the tissue sample, i.e. the tissue sample is effectively transparent to light from the light source. Preferably, the light will be visible light and may include ultraviolet and infrared light. More specifically, this light can be configured as either a first light beam having a substantially circular cross section, or as a second light beam having a slit like cross section. In both cases, the light beam is initially directed along the optical path and through the base window to illuminate the tissue sample. Depending on which light beam is used, however, the light beam will take different paths after it has transited through the tissue sample.

An optical detector, such as a charge-coupled device (CCD), is positioned on the optical path outside the housing window to receive light in the first light beam after is has passed through (transited) the tissue sample on the pedestal.

The transmitted light in this first beam can then be used for a wavefront analysis wherein refractive properties of the tissue sample are measured. The same optical detector, or a separate optical detector if desired, can also be used to analyze light of the second light beam after it has passed through the tissue cell.

When light in the second light beam is to be analyzed, the housing of the sample cell will also have at least one side window in addition to the housing window. The side window in this case will be distanced from the main optical path and will be oriented at an angle, $\alpha$, from the optical axis. Thus, the optical detector will receive the second light beam through the side window after it has been scattered off-axis from the main optical path by the tissue sample. When the slit configuration of the second beam has a length that is about the same as the breadth of the tissue sample, and has a width that is approximately equal to the depth of the tissue sample, the light that is scattered off-axis by the tissue sample can be effectively used to take dimensional measurements of the tissue sample. For each light beam, i.e. the first and second light beams, the optical detector(s) is(are) connected with a computer which will transform the optical measurements that are obtained into results which can be used to assess and evaluate the tissue sample.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
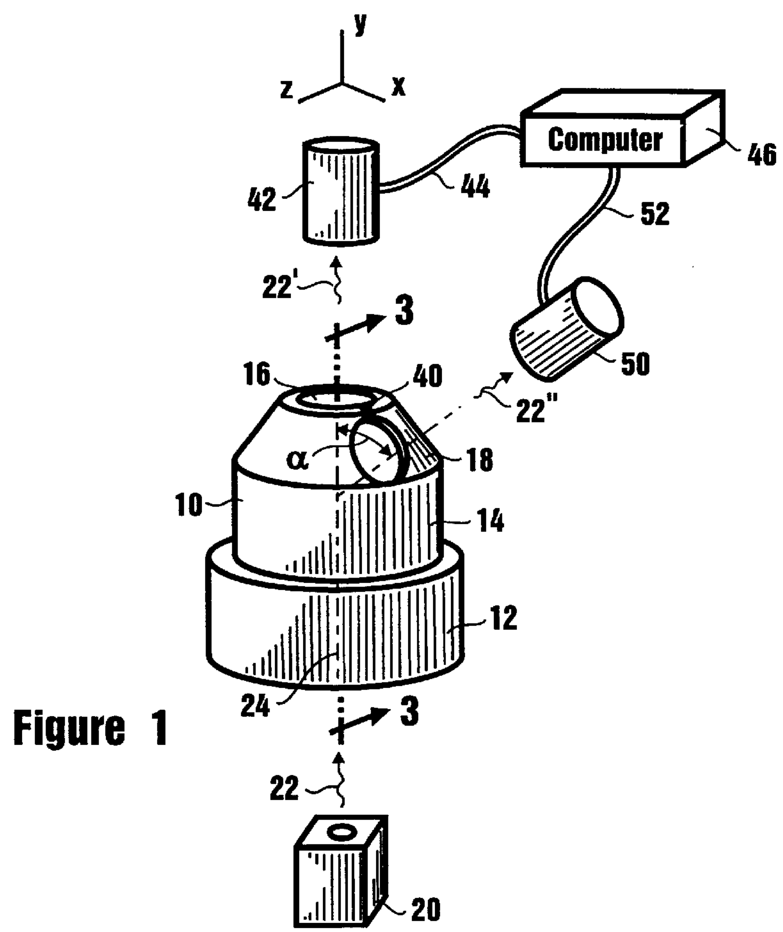
FIG. 1 is a perspective view of the sample cell of the present invention shown in combination with associated system components for evaluating donor corneal tissue.

Referring initially to FIG. 1, a sample cell in accordance with the present invention is shown and is designated 10. As shown, the sample cell 10 includes a base member 12 which is engaged with a housing 14. Further, it can be seen that the housing 14 is formed with both a housing window 16 and a side window 18. As intended for the present invention, both the housing 14 and base member 12 can be made of a molded plastic or of any other material that is suitable for the purposes of the present invention. In any case, it is important that both the housing window 16 and the side window 18 be transparent to the light that emanates from the light source 20. In the specific case where the housing 14 and base member 12 are made of an optical grade plastic, the housing window 16 and the side window 18 can be made integral with the housing 14. Also, it is to be appreciated that the side window 18 which is shown in FIG. 1 is only exemplary. Additional side windows 18 can be provided, as desired.

Preferably, the light from light source 20 is in the visible range and, depending on the particular measurements to be taken, can include also ultraviolet and infrared radiation. Further, as will be appreciated by the skilled artisan, depending on the particular tests to be performed, the light from light source 20 may be polarized or non-polarized, it may be collimated or non-collimated, and it may or may not be sheared. In sum, the particular characteristics of the light from light source 20 will be dictated by the requirements of the particular test and measurements to be taken.

Still referring to FIG. 1 it will be seen that the light beam 22 which emanates from the light source 20 is initially directed along an optical path 24. This optical path 24 extends through the sample cell 10 and through the housing window 16. The side window 18, however, is not positioned on the optical path 24. Instead, the side window 18 is distanced from the optical path 24 and is inclined at an angle, $\alpha$, to the optical path 24. Stated differently, after passing through the tissue sample 32, the light beam 22' passes through the housing window 16 on the optical path 24 and, as shown, the optical path 24 is substantially perpendicular to the housing window 16. On the other hand, after being scattered by the tissue sample 32, the light beam 22" passes through side window 18 on a path that is inclined at the angle $\alpha$ relative to the optical path 24. For purposes of the present invention, the angle $\alpha$ will preferably be about thirty five degrees and be in a range between approximately twenty degrees and approximately fifty degrees.

Figure 2:
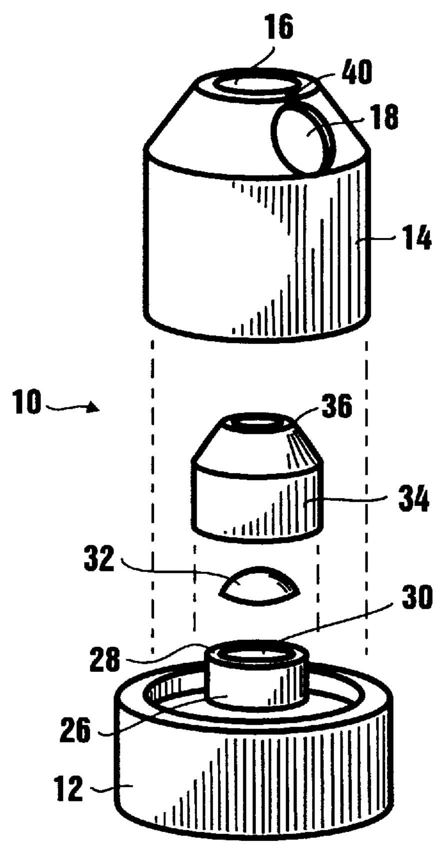
FIG. 2 is an exploded perspective view of the sample cell of the present invention.

Referring now to FIG. 2, the structure of the sample cell 10 is shown in more detail. Specifically, in FIG. 2 it can be seen that the base member 12 is formed with a pedestal 26 which projects from the base member 12. Further, the pedestal 26 is formed with a ridge 28 which surrounds a base window 30. As shown, the base window 30 provides a surface on which a tissue sample 32 can be placed. For the general purposes of the present invention, the tissue sample 32 can be considered to be a nucleated cornea which is to be assessed and evaluated for possible use in transplant surgery.

Still referring to FIG. 2, it will be seen that sample cell 10 also includes a retainer ring 34 which is formed with an inwardly inclined lip 36. With this structure, when the tissue sample 32 is position on the surface of base window 30, and the retainer ring 34 is engaged with the pedestal 26, the lip 36 will help retain the tissue sample 32 on the pedestal 26. Importantly, as indicated above, the tissue sample 32 is retained (not restrained) on the base window 30 with a "non-influencing" structure. This "non-influencing" structure, such as the combination pedestal 26 retainer ring 34, does not impose deforming or otherwise shape-altering forces on the tissue sample 32.

As also indicated in FIG. 2, the housing 14 is engageable with the base member 12. When so engaged, the base member 12 and the housing 14 together form a fluid chamber 38. For purposes of the present invention, it is preferable that the retainer ring 34 be dimensioned with respect to the pedestal 26 so that the two can be held together with what is commonly referred to as an interference fit. Similarly, the housing 14 is preferably dimensioned with respect to the base member 12 so that the two are held together with an interference fit. When assembled in this manner, the tissue sample 32 is retained on the pedestal 26 inside the fluid chamber 38.

Figure 3:
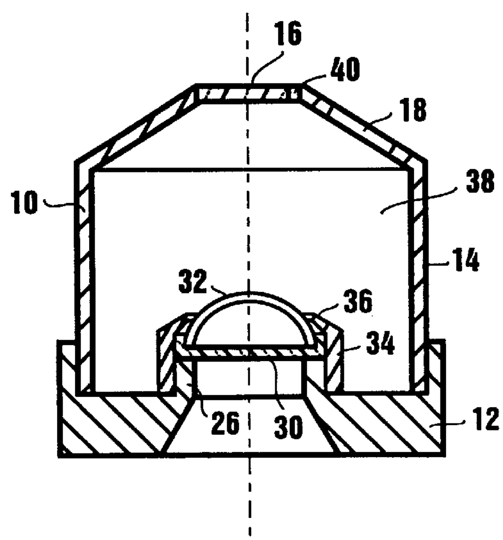
FIG. 3 is a cross sectional view of the sample cell as seen along the line 3—3 in FIG. 1.

An assembled sample cell 10 is, perhaps, best appreciated with reference to FIG. 3. In FIG. 3 it is seen that the pedestal 26 projects into the fluid chamber 38. Consequently, when the chamber 38 is filled with a fluid, such as a saline solution, the tissue sample 32 will be bathed in the solution and thereby preserved, at least temporarily. In order to fill the fluid chamber 38, as desired, and to provide for the removal of unwanted gases in the chamber 38, a vent 40 is formed into the housing 14.

In operation, a tissue sample 32 is positioned on the surface of base window 30, and a retainer ring 34 is engaged with the pedestal 26 of base member 12. The housing 14, which has been filled with a fluid, is then engaged with the base member 12 to create the sample cell 10 as shown in FIG. 1 and FIG. 3. The sample cell 10, with the tissue sample 32 held therein, can then be stored as desired until the tissue sample 32 is to be assessed and evaluated for possible use in transplant surgery. As envisioned by the present invention, this assessment and evaluation of the tissue sample 32 can require at least two differently configured light beams 22, and possibly more, depending on the nature of the tests that are involved. For purposes of the present invention, a first light beam 22 will be taken to have a generally circular cross section. On the other hand, a second light beam 22 is taken to be configured as a slit which has a length and a width.

By cross referencing FIG. 1 with FIG. 3, it can be appreciated that when the first light beam 22 (circular cross section) is directed along the optical path 24 toward the sample cell 10, it will pass through the base window 30 and be incident on the tissue sample 32. The light will then emerge from the tissue sample 32 and continue along the optical path 24 as the light beam 22' which will pass from the sample cell 10 through the housing window 16 and be received by the optical detector 42. For purposes of the present invention, the optical detector 42 is preferably a charge-coupled device (CCD) of a type well known in the pertinent art. Optical detector 42, however, may be any type of device that is well known as being suitable for the particular purpose.

Figure 4:
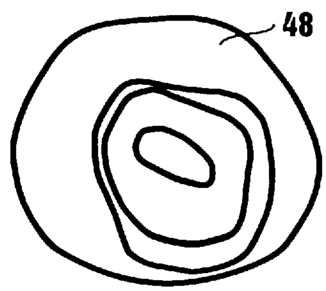
FIG. 4 is a plan view of an exemplary refractive topography map of the donor corneal tissue.

FIG. 1 also shows that the optical detector 42 is connected via a line 44 to a computer 46. As one example of the results to be obtained with this combination of elements, the computer 46 can be programmed to evaluate the Optical Path Differences (OPD) between the wavefront in light beam 22' that is generated by the tissue sample 32 and the desired wavefront of an idealized cornea. Specifically, the OPD can be determined using techniques well known in the pertinent art. For example, using fitting algorithms such as Zernike polynomials, or Legendre polynomials, or Tayler polynomials, it is possible to model the tissue sample 32. For this purpose, the result is an optical profile map 48 (a corneal topography map) such as the exemplary one shown in FIG. 4. In addition to the refractive properties of the tissue sample 32 that can be deduced from the optical profile map 48, it is also possible when analyzing light beam 22', to determine the presence of optically significant opacities and to observe optical characteristics of the tissue sample 32 which can be used to give some insight into the aging of the tissue sample 32.

Still cross referencing FIG. 1 and FIG. 3, it can be appreciated that when a second light beam 22 is directed through the sample cell 10, light can be scattered off-axis by the tissue sample 32 so that it will emerge from the tissue sample 32 as a light beam 22". As shown, the light beam 22" includes light that is scattered from the tissue sample 32 and directed toward the side window 18. Further, as shown in FIG. 1, the light beam 22" is received by an optical detector 50 which is connected with the computer 46 via a line 52. Although two optical detectors 42, 50 are shown for use with the sample cell 10, it will be appreciated by the skilled artisan, that only one optical detector can be used alternatively, or more than two optical detectors can be used, if necessary.

Figure 5B:
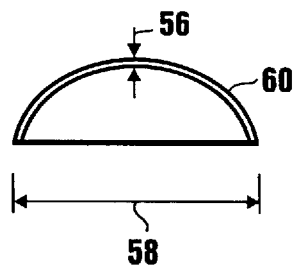
FIG. 5B is a cross sectional view of the donor corneal tissue as seen along the line 5B—5B in FIG. 5A.
Figure 5A:
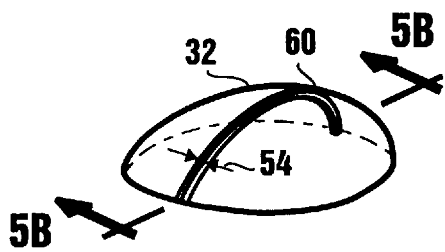
FIG. 5A is a perspective view of a donor corneal tissue with a region of the tissue identified as being illuminated with a slit light beam in accordance with the present invention.

For the specific situation wherein the second light beam 22 is structured as a slit, it is preferable for the width 54 of the slit (see FIG. 5A) to be approximately equal to, or less than, the depth 56 of the tissue sample 32 (see FIG. 5B). Further, it is preferable for the length of the slit to exceed the breadth 58 of the tissue sample 32 (see FIG. 5B). With these dimensions, the light beam 22" will include scattered light from a region 60 of the tissue sample (FIGS. 5A and 5B) which can be effectively used for measuring dimensions of the tissue sample 32. With specific reference to FIG. 1 it will be appreciated that the region 60 of tissue sample is illuminated by a second light beam 22 which is aligned substantially in the y-z plane. The optical detector 50, however, will be viewing the region 60 in the x-y plane from a direction that is equal to the angle a from the optical path 24.

While the particular Optical Donor Tissue Cell as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A sample cell for use in imaging a tissue sample which comprises:

- a base member formed with a pedestal, said pedestal having a base window;
- a retainer ring engageable with said pedestal to retain the tissue sample on said pedestal and to establish an optical path through said base window and through said tissue sample;
- a housing formed with a housing window, said housing being engageable with said base member to create a fluid chamber therebetween, with said pedestal extending into said chamber;
- a light source for directing a light beam along said optical path to illuminate the tissue sample through said base window; and
- an optical detector for receiving said light beam through said housing window after said light beam transits through the tissue sample on said pedestal.

2. A sample cell as recited in claim 1 further comprising a computer means connected with said optical detector for analyzing said light beam received by said optical detector.

3. A sample cell as recited in claim 2 wherein said housing window is located on said optical path and said optical detector receives light transmitted through the tissue sample and thorough said housing window for analysis by said computer means.

4. A sample cell as recited in claim 2 wherein said housing further comprises at least one side window, said side window being distanced from said optical path and oriented at an angle, $\alpha$, thereto, and wherein said optical detector receives light scattered by said tissue sample through said side window for analysis by said computer means.

5. A sample cell as recited in claim 4 wherein said tissue sample has a breadth and a depth and wherein said light source creates a slit light beam having a length and a width with said length of said slit light beam extending across said breadth of said tissue sample and said width of said slit light beam approximately equal to said depth of said tissue sample.

6. A sample cell as recited in claim 1 wherein said light in said light beam has a wavelength and said sample cell further comprises a shearing waveplate for effectively increasing said wavelength of said light beam.

7. A sample cell as recited in claim 6 wherein said wavelength of light in said light beam is within a spectrum from ultra-violet to infra-red.

8. A sample cell as recited in claim 1 wherein said light in said light beam is collimated.

9. A sample cell for use in imaging a tissue sample which comprises:

a means for holding the tissue sample in a predetermined position;

a means for selectively directing a first light beam along an optical path for transmission through the tissue sample, said first light beam having a cross section wherewith said first light beam illuminates substantially all of the tissue sample;

a means for separately directing a second light beam toward the tissue sample along said optical path, said second light beam being configured as a slit having a length and a width to illuminate a predetermined portion of the tissue sample;

a means positioned on said optical path for detecting light of said first light beam after said first light beam has been transmitted through the tissue sample along said optical path; and a means positioned off said optical path for detecting light of said second light beam after said second light beam has been scatted by the tissue sample off the optical path.

10. A sample cell as recited in claim 9 wherein said holding means comprises:

a base member formed with a pedestal, said pedestal having a base window;

a retainer ring engageable with said pedestal to retain the tissue sample on said pedestal and to establish an optical path through said base window, through said tissue sample and through said retainer ring; and a housing formed with a housing window, said housing being engageable with said base member to create a fluid chamber therebetween, with said pedestal extending into said chamber.

11. A sample cell as recited in claim 10 wherein said housing window is located on said optical path and said means for detecting said first light beam receives light transmitted through the tissue sample and thorough said housing window.

12. A sample cell as recited in claim 11 wherein said housing further comprises at least one side window, said side window being distanced from said optical path and oriented at an angle, $\alpha$, thereto, and wherein said means for detecting said second light beam receives light scattered by said tissue sample through said side window.

13. A sample cell as recited in claim 12 wherein said tissue sample has a breadth and a depth and wherein said length of said second light beam extends across said breadth of said tissue sample and said width of said second light beam is approximately equal to said depth of said tissue sample.

14. A sample cell as recited in claim 13 wherein said wavelengths of light in respective said first and second light beams are each within a spectrum from ultra-violet to infra-red.

15. A sample cell as recited in claim 13 wherein said light in said first and second light beams is collimated.

16. A method for imaging a tissue sample which comprises the steps of:

holding the tissue sample in a predetermined position;

selectively directing a first light beam along an optical path for transmission through the tissue sample, said first light beam having a cross section wherewith said first light beam illuminates substantially all of the tissue sample;

separately directing a second light beam toward the tissue sample along said optical path, said second light beam being configured as a slit having a length and a width to illuminate a predetermined portion of the tissue sample;

selectively positioning an optical detector on said optical path for detecting light of said first light beam after said first light beam has been transmitted through the tissue sample along said optical path; and separately positioning an optical detector off said optical path for detecting light of said second light beam after said second light beam has been scatted by the tissue sample off the optical path.

17. A method recited in claim 16 wherein said holding step further include the steps of:

placing the tissue sample on a pedestal, said pedestal being formed on a base member and having a base window;

engaging a retainer ring with said pedestal to retain the tissue sample on said pedestal and to establish an optical path through said base window, through said tissue sample, and through said retainer ring; and placing a housing formed with a housing window on said base member to create a fluid chamber therebetween, with said pedestal extending into said chamber.

18. A method as recited in claim 17 further comprising the step of connecting a computer with any said optical detector for analyzing said light beam received by said optical detector.

19. A method as recited in claim 18 wherein said housing window is located on said optical path and said first light beam passes therethrough, and wherein said housing further comprises at least one side window, said side window being distanced from said optical path and oriented at an angle, $\alpha$, thereto, and said second light beam through said side window.

20. A method as recited in claim 18 wherein said tissue sample has a breadth and a depth and wherein said length of said second light beam extends across said breadth of said tissue sample and said width of said second light beam is approximately equal to said depth of said tissue sample.

* * * * *

UNITED STATES PATENT AND TRADEMARK OFFICE

CERTIFICATE OF CORRECTION

PATENT NO. : 6,256,089 B1
DATED : July 3, 2001
INVENTOR(S) : Phillip C. Baker

It is certified that error appears in the above-identified patent and that said Letters Patent is hereby corrected as shown below:

Column 4,
Line 50, delete [26 retainer] insert -- 26/retainer --.

Column 6,
Line 19, delete [a] insert -- $\alpha$ --

Signed and Sealed this

Nineteenth Day of February, 2002

*Attest:*

JAMES E. ROGAN

*Attesting Officer*

*Director of the United States Patent and Trademark Office*